(12) United States Patent
Zhou et al.

(10) Patent No.: US 6,979,452 B2
(45) Date of Patent: Dec. 27, 2005

(54) LOW PH, HIGH SKIN FRICTION COSMETIC CREAMS

(75) Inventors: Yan Zhou, Montville, NJ (US);
Ramesh Surianarayanan, Mumbai (IN); Prem Chandar, Closter, NJ (US); Pushker Sona, Mumbai (IN); Michael J. Barratt, Oak Ridge, NJ (US)

(73) Assignee: Unilever Home & Personal Care USA division of Conopco, Inc., Greenwich, CT (US)

( * ) Notice: Subject to any disclaimer, the term of this patent is extended or adjusted under 35 U.S.C. 154(b) by 74 days.

(21) Appl. No.: 10/104,464

(22) Filed: Mar. 22, 2002

(65) Prior Publication Data

US 2003/0180334 A1    Sep. 25, 2003

(51) Int. Cl.[7] ............................ A61K 7/00; A61K 9/14; A61K 9/50
(52) U.S. Cl. .................. 424/401; 424/489; 424/502
(58) Field of Search ................ 424/401, 489, 424/502

(56) References Cited

U.S. PATENT DOCUMENTS

| | | | |
|---|---|---|---|
| 3,867,549 A | 2/1975 | Costello et al. | 424/361 |
| 3,944,506 A | 3/1976 | Hramchenko et al. | 252/526 |
| 4,536,519 A | 8/1985 | Suzuki et al. | 514/785 |
| 5,599,549 A * | 2/1997 | Wivell et al. | 424/401 |
| 6,036,966 A | 3/2000 | Youssefyeh | 424/401 |
| 6,063,366 A * | 5/2000 | Sugai et al. | 424/69 |
| 6,153,177 A | 11/2000 | Bartolone et al. | 424/62 |

FOREIGN PATENT DOCUMENTS

| | | |
|---|---|---|
| EP | 0 775 486 A1 | 5/1997 |
| GB | 1 303 566 | 1/1973 |
| WO | 01/70187 | 9/2001 |
| WO | 01/70188 A1 | 9/2001 |
| WO | 02/067889 A2 | 9/2002 |

OTHER PUBLICATIONS

Percutaneous Penetration Enhancers, CRC Press, 1995, p. 407.
Laufer et al. "Objective Measurement and Self-Assessment of Skin-Care Treatments", Cosmetics and Toiletries Magazine, vol. 111, Jun. 1996, pp. 92-96.
*International Search Report No. PCT/EP 03/02056 dated Jul. 11, 2003, 4 pp.*
Falbe J, Regitz M: "Rompp Chemie Lexikon" p. 3991, 1995, Thieme, Stuttgart, Germany—1 page.
WPI ACC. No. 1997-282926/199726 Derwent abstract of EP 0 775 486—1 page.

* cited by examiner

*Primary Examiner*—Shengjun Wang
(74) *Attorney, Agent, or Firm*—Ellen Plotkin

(57) ABSTRACT

A high skin friction cosmetic composition that can provide the consumer-desired sensory properties of traditional vanishing creams, stable at low pH, containing solid asymmetric particles and an anionic emulsifier having pKa values of less than about 4.5. The composition preferably further includes an acidic skin benefit agent. A method of controlling or preventing an oily skin appearance and/or feel especially in the facial area, by applying to the skin the inventive composition is also disclosed.

18 Claims, No Drawings

LOW PH, HIGH SKIN FRICTION COSMETIC CREAMS

FIELD OF THE INVENTION

The invention relates to cosmetic skin creams having low pH and providing a high skin friction.

BACKGROUND OF THE INVENTION

Consumers living in hot, humid climates, or consumers with oily skin, desire cosmetic products that have unique tactile properties during use. Specifically, such products should, upon application to the skin, deliver a high skin friction and a matte finish to overcome the oily skin feel and shiny skin appearance. The greater the increase in skin friction, the less greasy the user perceives the product to be. See Laufer et al., Objective Measurement and Self-Assessment of Skin-Care Treatments, Cosmetics and Toiletries Magazine, Vol. 111, June 1996, pp. 92–96.

More specifically, the typical sensory and optical features of these high skin friction and matte finish creams, also known as vanishing creams, are: 1) provide a dry, draggy, non-greasy feel to skin; 2) provide a non-shiny, matte finish; 3) spread easily on the skin; 4) absorb or "vanish" rapidly into the skin. The traditionally used vanishing creams contain high levels of stearic acid and alkaline metal soap as an emulsifier, which is important to physical stability of the product. The soap is formed by the in situ neutralization with caustic potash or other alkali on a portion of the stearic acid. Consequently, the creams made by saponification of stearic acid have a pH limit, i.e., greater than 5.7, in order to maintain the right balance of acid and acid soap. The anionic soap becomes inactive in acidic conditions in which hydrolysis occurs, resulting in undissociated stearic acid, and therefore causes physical stability problem at low pH.

The lack of physical stability of the acid soap emulsified vanishing creams at low pH is a disadvantage that restricts the use therein of valuable acidic benefit actives, such as alpha-hydroxy carboxylic acids, because the acidic actives reduce the pH of the compositions. However, emerging trends in skin care have required that vanishing cream formulations be adapted to incorporate acidic skin benefit agents. U.S. Pat. No. 6,153,177 (Bartolone et al.) discloses vanishing creams containing acid soap which have a pH above 5 and, therefore, include alkali or alkaline earth metal salts of alpha-hydroxy acid (AHA) to achieve skin lightening benefit. Care was taken not to include the acid form of AHA into the formulation in order to avoid destabilization of the base by the acid for the reasons stated above. However, it is generally accepted that actives in their acidic form penetrate the skin better than their ionized, and salt or electrolyte tends to affect the sensory feel of soap-based vanishing cream form. See *Percutaneous Penetration Enhancers,* CRC press, pp. 407 (1995). Therefore, it was clear that further work was necessary in order to enhance the performance of vanishing creams in delivery of acidic skin benefit agent, while maintaining the sensory attributes of traditional vanishing creams.

WO 01/70187 (Dwiwahyu et al.) disclose low pH (2–4.8), non-acid soap vanishing cream with enhanced skin benefit properties. A C8–C22 fatty acid substituted saccharide is used to stabilize the low pH stearic acid-based vanishing cream. Although these compositions are said to deliver an acidic skin benefit agent, the sensory characteristics of traditional vanishing creams have not been realized, which is believed to be due to the lack of a proper emulsifier system.

U.S. Pat. No. 4,536,519 (Suzuki, et al) discloses emulsified cosmetic compositions, including vanishing cream, using a neutralized phosphoric acid ester as an emulsifier, a nonionic surfactant with HLB<6 and fatty components including natural oil, wax, fat, and fatty acid or alcohol at pH of neutral to weakly acidic. These compositions, however, lack the sensory characteristics of traditional vanishing creams, and that is believed to be due to the lack of a proper emulsifier system.

Therefore, there is a need to provide a pH insensitive and stable cosmetic composition which not only maintains the unique sensory characteristics of vanishing cream but also enable to incorporate pH sensitive skin benefit agents.

SUMMARY OF THE INVENTION

The shortcomings of the prior art are overcome with compositions that can provide the consumer-desired sensory properties of traditional vanishing creams, stable at low pH, that go beyond the pH tolerance range of an acid soap formulation. The present invention includes a cosmetic composition comprising:
  (a) at least about 4% by weight of the composition of solid asymmetric particles;
  (b) an anionic emulsifier selected from the group consisting of alkyl sulphates, aralkyl sulphates, alkyl ethoxy ether sulphates, alkaryl sulphonates, alkyl succinates, alkyl sulphosuccinates, N-alkoyl sarcosinates, isethionates, N-acyl taurate, fatty acid amides of methyl tauride and combinations thereof; and
  (c) a cosmetically acceptable vehicle;
  wherein the pH of the composition is less than about 5.7 and
  wherein the composition has a normal stress of less than minus about 100 milli-Newtons.

The composition may further contain acidic skin benefit agents. Skin benefit agents for purposes of the present invention include alpha-hydroxy carboxylic acids, beta-hydroxy carboxylic acids, poly-hydroxy carboxylic acids, and mixtures thereof. Examples of alpha-hydroxy carboxylic acids are glycolic acid, lactic acid, 2-hydroxyoctanoic acid, and mixtures thereof. An example of beta-hydroxy carboxylic acid is salicylic acid. Other acidic skin benefit agents include ferulic acid and sebacic acid.

The present invention also includes a method of controlling or preventing an oily skin appearance and/or feel especially in the facial area, by applying to the skin the inventive composition.

DETAILED DESCRIPTION OF THE INVENTION

Except in the operating and comparative examples, or where otherwise explicitly indicated, all numbers in this description indicating amounts of material or conditions of reaction, physical properties of materials and/or use are to be understood as modified by the word "about." All amounts are by weight of the final composition, unless otherwise specified.

As used herein, the term "comprising" means including, made up of, composed of, consisting and/or consisting essentially of.

The term "skin" as used herein includes the skin on the face, neck, chest, back, arms, hands, legs and scalp.

The term "solid" as used herein means that the material is not fluid at 25° C.

The term "fluid" as used herein means that the material is fluid at 25° C.

In order to provide the consumer-desired sensory properties of traditional vanishing creams, stable at low pH, that go beyond the pH tolerance range of an acid soap formulation the cosmetic compositions of the present invention include:

(a) at least about 4% by weight of the composition of solid asymmetric particles;

(b) an anionic emulsifier selected from the group consisting of alkyl sulphates, aralkyl sulphates, alkyl ethoxy ether sulphates, alkaryl sulphonates, alkyl succinates, alkyl sulphosuccinates, N-alkoyl sarcosinates, isethionates, N-acyl taurate, fatty acid amides of methyl tauride and combinations thereof; and (c) a cosmetically acceptable vehicle;

wherein the pH of the composition is less than about 5.7 and wherein the composition has a normal stress of less than minus about 100 milli-Newtons.

Preferably, the asymetric particles are platelike, such that upon application to skin, the particles align under shear to produce the negative normal stress that is perceived as a dry and draggy feel on the skin surface. Preferred platelike asymetric particles are fatty acid crystals.

The product consistency is also achieved through the use of pH-stable structurants to replace the acid soap network. The anionic emulsifiers referred to above are such pH-stable structurants and are capable to remain as anionic at low pH to stabilize the system, as well as non-ionic emulsifiers that may optionally be used in combination with the anionic emulsifiers.

The composition may further contain acidic skin benefit agents. Skin benefit agents for purposes of the present invention include alpha-hydroxy carboxylic acids, beta-hydroxy carboxylic acids, poly-hydroxy carboxylic acids, and mixtures thereof. Examples of alpha-hydroxy carboxylic acids are glycolic acid, lactic acid, 2-hydroxyoctanoic acid, and mixtures thereof. An example of beta-hydroxy carboxylic acid is salicylic acid. Other acidic skin benefit agents include ferulic acid and sebacic acid.

The present invention also includes a method of controlling or preventing an oily skin appearance and/or feel especially in the facial area, by applying to the skin the inventive composition.

Asymmetric Particles

The inventive compositions employ asymmetric solid particles, to impart a cream-like viscosity. Furthermore, by virtue of being asymmetric, the particles deliver high skin friction. Suitable solid particles include fatty acid crystals, mica, talc, clays and mixtures thereof. The preferred solid particles are selected from the fatty acid crystals wherein fatty acid contains from 12–22 carbon atoms, because they are inexpensive and the most aesthetically acceptable. The most preferred fatty acid is stearic acid. The inventive compositions contain at least 4% of the asymmetric solid particles, preferably at least 10%, more preferably from 10% to 25%, most preferably from 12% to 20% to obtain the best feel, appearance, and viscosity. The exact amount depends on the final composition and the nature of the other ingredients in the composition. The amount of the asymmetric solid particles, however, must be sufficient to impart the vanishing cream-like consistency to the composition, i.e. having the viscosity profiles at three defined shear rates as specified below under the defined measurement conditions.

Viscosity Profile of Vanishing Creams

The inventive compositions have viscosity profiles of vanishing creams at three defines shear rates:

| | |
|---|---|
| (1) about 10 to about 75 Pascal-seconds (PaS) | at a shear rate of 1 reciprocal second ($s^{-1}$), |
| (2) about 2 to about 25 Pas | at a shear rate of 10 $s^{-1}$, and |
| (3) about 0.6 to about 5 PaS | at a shear rate of 100 $s^{-1}$. | in order to provide a cream consistency that can be rubbed in easily. Preferably the viscosity profiles are:

| | |
|---|---|
| (1a) about 15 to about 60 PaS | at a shear rate of 1 $s^{-1}$, |
| (2a) about 2.5 to about 15 PaS | at a shear rate of 10 $s^{-1}$, and |
| (3a) about 0.8 to about 3 PaS | at a shear rate of 100 $s^-$. |

Most preferably, the viscosity profile is:

| | |
|---|---|
| (1b) about 20 to about 50 PaS | at a shear rate of 1 $s^{-1}$, |
| (2b) about 3 to about 7 PaS | at a shear rate of 10 $s^{-1}$, and |
| (3b) about 1 to about 2 PaS | at a shear rate of 100 $s^{-1}$. |

The procedure for measuring viscosity is as follows:

Viscosity is measured using a rheometer with a shearing force capability and normal force transducer (e.g. ARES (Advanced Rheometric Expansion System) from Rheometrics). Samples are compressed between parallel plates of a diameter 25 mm and gap (distance between two plates) of 100 microns. The measurements are made in a shear sweep mode with a shear rate range from 0 to 10,000 sec–1. Measurements are conducted at room temperature and pressure.

In the inventive compositions, the solid asymmetric particles are dispersed in water. Acidic skin benefit agents and anionic surfactants are employed in such amount as to provide a desired skin benefit and yet to not compromise the high skin friction of the inventive compositions.

Skin Friction/Normal Stress

The skin friction is measured by normal stress. Normal stress is the force exerted by the material in the axial direction during shearing flow. Normal stresses arise when the material (product) microstructure becomes anisotropic under flow. Negative normal stresses are generated by a decrease in bulk "volume" such as shear-induced ordering. Materials exhibiting this behavior are crystalline phases (e.g. fatty acids), rods, platelets, liquid crystals, and surfactant lamellar mesophases.

Measurement Procedure:

Normal force is measured using a rheometer with a shearing force capability and normal force transducer (e.g. ARES (Advanced Rheometric Expansion System) from Rheometrics). Samples are compressed between parallel plates of a diameter 25 mm and gap (distance between two plates) of 100 microns. The measurements are made in a shear sweep mode with a shear rate range from 0 to 10,000 sec–1. The normal stress value was calculated as the difference between the force at zero shear rate and force at highest shear rate. A negative difference of less than −100 milli-Newtons is correlated to products/materials with the draggy sensation (high skin friction). Measurement is conducted at room temperature (about 20 to about 25 C).

The inventive compositions have the normal stress of less than about minus 100 milli-Newtons; preferably less than minus 200 milli-Newtons; most preferably, in order to obtain the most desired high skin friction, less than about minus 100 milli-Newtons; e.g. from about minus 200 milliNewtons to about minus 2000 milli-Newtons.

Anionic Emulsifiers

Anionic emulsifiers suitable for use in accordance with the invention have a pKa in their acid form of less than about 5.7 and correspond to formula (I):

RYX    (I), in which

R is an alkyl and/or alkenyl aralkyl, alkarylradical containing 6 to 30 carbon atoms, Y is the hydrophilic anionic head group, and X is an alkali metal and/or alkaline earth metal, ammonium, alkylammonium, alkanolammonium or glucammonium.

Preferred anionic emulsifiers are those which remain anionic at low pH, having pKa values of less than about 5.7

Preferred anionic emulsifiers include salts (including, for example, sodium, potassium, ammonium, and substituted ammonium salts such as mono-, di- and triethanolamine salts) of the anionic sulfate, sulfonate and sarcosinate emulsifiers.

Other preferred anionic emulsifiers also include the isethionates such as the acyl isethionates, N-acyl taurates, fatty acid amides of methyl tauride, alkyl succinates and sulfosuccinates, monoesters of sulfosuccinate (especially saturated and unsaturated $C_{12}$–$C_{18}$ monoesters, such as sodium oleyl succinate, ammonium lauryl sulphosuccinate.), diesters of sulfosuccinate (especially saturated and unsaturated $C_6$–$C_{18}$ diesters), N-acyl sarcosinates.

Anionic Sulfate Emulsifier

Anionic sulfate emulsifiers suitable for use herein include the linear and branched primary alkyl sulfates, alkyl ethoxysulfates, fatty oleyl glycerol sulfates, alkyl phenol ethylene oxide ether sulfates, the $C_5$–$C_{17}$ acyl N—($C_1$–$C_4$ alkyl) and —N—($C_1$–$C_2$ hydroxyalkyl) glucamine sulfates, and sulfates of alkylpolysaccharides such as the sulfates of alkylpolyglucoside, and combinations thereof, especially their sodium, magnesium, ammonium and mono-, di- and triethanolamine salts. The alkyl groups generally contain from 6 to 30 carbon atoms and are preferably fatty alkyl groups. The alkyl ethoxy ether sulphates may contain from 1 to 30 ethylene oxide or propylene oxide units per molecule, and preferably contain 2 to 10 ethylene oxide units per molecule. Preferred examples include, sodium cetyl sulfate, sodium lauryl sulfate, sodium stearyl sulfate, sodium lauryl ether sulfate, ammonium lauryl sulfate, triethanolamine lauryl sulfate, sodium C14–16 olefin sulfonate, ammonium pareth-25 sulfate (ammonium salt of a sulfated polyethylene glycol ether of a mixture of synthetic C12–15 fatty alcohols), sodium myristyl ether sulfate, ammonium lauryl ether sulfate.

Anionic Sulfonate Emulsifier

Anionic sulfonate emulsifiers suitable for use herein include the salts of $C_5$–$C_{20}$ linear alkylbenzene sulfonates, alkyl ester sulfonates, $C_6$–$C_{22}$ primary or secondary alkane sulfonates, $C_6$–$C_{24}$ olefin sulfonates, alkyl glycerol sulfonates, fatty acyl glycerol sulfonates, fatty oleyl glycerol sulfonates, and any mixtures thereof. Preferred examples include, sodium dodecylbenzene sulfonate and triethanolamine dodecylbenzene sulfonate.

Anionic Sarcosinate Emulsifier

Other suitable anionic surfactants are the alkali metal sarcosinates of formula

R—C(O)N($R^1$)$CH_2$COOM, wherein R is a $C_5$–$C_{20}$ linear or branched alkyl or alkenyl group, $R^1$ is a $C_1$–$C_4$ alkyl group and M is an alkali metal ion. Preferred examples are the myristyl and oleyl methyl sarcosinates, sodium N-lauroyl sarcosinate in the form of their sodium salts.

The most preferred anionic surfactants are sodium cetyl sulphate, sodium stearyl sulfate, triethanolamine lauryl sulphate, sodium lauryl ether sulphate mono-ethylene-oxide, sodium lauryl ether sulphate di-ethylene-oxide, sodium lauryl ether sulphate tri-ethylene-oxide, ammonium lauryl sulphate and ammonium lauryl ether sulphate mono-ethylene-oxide, ammonium lauryl ether sulphate di-ethylene-oxide, and ammonium lauryl ether sulphate tri-ethylene-oxide and mixtures thereof.

Amounts of anionic emulsifier in the composition are in the range of about 0.1 to about 10% by weight, preferably about 0.5% to about 5%, more preferably about 0.75% to about 3%.

Nonionic Emulsifiers and Ratio to Anionic Emulsifiers

Selected nonionic emulsifiers may be also optionally, but preferably, included. Nonionic emulsifiers are preferably solid and preferably have a mono fatty alkyl group containing 12 to 20 carbon atoms, preferably containing 14 to 18 carbon atoms, and preferably saturated. Examples of nonionic emulsifiers include the following, either alone or in combination:

ethoxylated alkyl ether, available commercially from ICI, Wilmington, Del., under the trade name Brij, such as the Brij series polyoxylene alkyl ether containing an alkyl chain of at least C12;

sorbitan esters, for example the emulsifiers available commercially from ICI, Wilmington, Del., under the trade name Span, such as Span 60 or Span 40;

ethoxylated sorbitan esters, for example the emulsifiers available commercially from ICI, Wilmington, Del. under the trade name Tween, such as a polysorbate containing an alkyl chain of at least C12 such as Tween 60® or Tween 61®;

ethoxylated fatty acid esters such as ethoxylated stearates, for example the emulsifiers available commercially from ICI, Wilmington, Del., under the trade name MYRJ, such as the MYRJ® series polyethylene glycol (PEG) stearate; and fatty alcohol, ethoxylated fatty alcohols, esters of glycerin and fatty acids.

When nonionic emulsifiers are present, weight ratios of anionic emulsifiers to nonionic emulsifiers are set at a level such that the high friction skin cream compositions exhibit similar viscosity profiles under the three shear rates specified previously and that the compositions exhibit a normal force value less than minus 100 milli-Newton. Weight ratios of anionic to nonionic emulsifiers may be 1:0000001 to 1:9, preferably, 3:2 to 1:7, most preferably, 1:1 to 1:4.

Acidic Skin Benefit Agents

Skin benefit agents may also be optionally, but preferably, included in the compositions of the present invention. Skin benefit agents are defined as active compounds that deliver a benefit to skin. For purposes of the present invention, acidic skin benefit agents refer to skin benefit agents that render the overall composition acidic while being more active in acidic form, as well as those that are more active in acidic conditions but do not themselves render the overall composition more acidic.

Examples of acidic skin benefit agents include alpha-hydroxy acids, beta-hydroxy acids, polyhydroxy acids, skin lightening agents, and mixtures thereof. Examples of preferred acidic skin benefit agents include glycolic acid, lactic acid, 2-hydroxyoctanoic acid, salicylic acid, ferulic acid and sebacic acid, or combinations thereof.

The amount of the acidic skin benefit agent is at least about 0.001% by weight of the composition.

Other Optional Skin Benefit Materials and Cosmetic Adjuncts

Hydrophobically modified polymeric emulsifiers may be optionally present in the inventive compositions as a co-structurent, typically with a trade name, Pamulen TR series, from 0.001 to 2% by weight, supplied by BFGoodrich Co., Cleverland, Ohio.

pH adjusting agents may be used to maintain the desired pH, if necessary, especially in the presence of certain acidic actives which may significantly lower the pH of the compositions. Preferred pH adjusting agents include inorganic or organic bases such as ammonium hydroxide, potassium hydroxide, sodium hydroxide and triethanolamine. Preferred pH adjusting agents also include inorganic acids such as hydrochloride acid.

Emollient materials (fluid oils) selected from the groups of silicone oils or synthetic esters may be incorporated into the compositions of the present invention. The oils are employed in such amount as to not compromise the high skin friction of the inventive compositions. They may be present in a weight ratio to the solid particles, i.e. fatty acids, such that the composition exibits a normal force value of less than −100 milli-Newton (mN) under the measurement condition defined previously. Weight ratio of emollient material to the solid particles may be less than 1.0. preferably, less than 0.5, most preferably, less than 0.2. Oily sunscreens, when used in the composition are considered to be emollient materials, and will be further discussed below.

Silicone oils may be included in the compositions as emollient materials. These are preferably chosen from cyclic or linear polydimethylsiloxanes containing from about 3 to about 9, preferably from about 4 to about 5, silicon atoms. Other silicone oils may be also included, such as polyalkyl siloxanes, polyalkylaryl siloxanes and polyether siloxane copolymers (e.g. dimethicone copolyol). The polyalkyl siloxanes useful herein include, for example, polydimethyl siloxanes with viscosities of from about 5 to about 100,000 centistokes at 25° C., preferably, polydimethyl siloxanes having viscosities from about 10 to about 400 centistokes at 25° C.

Suitable ester emollients include: esters of fatty acids or alcohols and hydrocarbons, preferably C8–C20 alkyl ester of fatty acids such as, isopropyl myristate, isopropyl palmitate, isostearyl palmitate, tridecyl salicylate, C12–15 octanoate and isopropyl stearate, or any mixtures thereof.

The oils may be employed singly or in mixtures with one another.

The inventive compositions most preferably further include an ingredient selected from the group consisting of antioxidants, reducing agents, chelating agents, and mixtures thereof to improve the stability of the cosmetic cream. These ingredients provide an additional level of protection against oxidation of skin benefit agents in the cosmetic cream. Common examples of antioxidants, reducing agents and chelating agent for the present formulations can be found in the CTFA International Cosmetic Ingredient Dictionary $4^{th}$ Edition, The Cosmetic, Toiletry, and Fragrance Association, Inc., Washington, D.C., 1991.

Preferable reducing agents are sodium sulfite, sodium bisulfite, sodium metabisulfite, sodium thiosulfite or other thiols, such as thioglycerol, thiourea, thioglycolic acid, cysteine and the like. Preferable antioxidants are rac-6-hydroxy-2,5,7,8-tetra-methylchromane-2-carboxylic acid (trolox), propyl gallate, n-propyl trihydroxybenzoate, t-butyl hydroquinone and butylated hydroxytoluene (BHT), butylated hydroxyanisole (BHA), tocopheryl acetate, ascorbyl palmitate, hydroquinone, dibutyl hydroquinone and the like.

Suitable examples of chelating agents include, but are not limited to, EDTA, citric acid, tartaric acid, organo aminophosphonic acids and organo phosphonic acid components including certain of the commercially available Dequest™ compounds, marketed by Monsanto. Preferred is 1-hydroxy-ethylene, (1.1-diphosphonic acid).

Organo aminophosphonic acid is an organic compound comprising of at least one phosphonic acid group, and at least one amino group. Suitable organo aminophosphonic acid components for use herein include the amino alkylene poly (alkylene phosphonic acids) and nitrilo trimethylene phosphonic acids. Examples of this type of organo aminophosphonic acid components include certain of the commercially available Dequest™ compounds, marketed by Monsanto.

Preferred are amino tri (methylene phosphonic acid) (Dequest 2006®), diethylene triamine penta (methylene phosphonic acid) and hexamethylene diamine tetra (methylene phosphonic acid).

Other suitable additional heavy metal ion sequestrants for use herein include nitrilotriacetic acid and polyaminocarboxylic acids such as ethylenediaminotetracetic acid, or ethylenetriamine pentacetic acid.

Still other suitable additional heavy metal ion sequestrants for use herein are iminodiacetic acid derivatives such as 2-hydroxyethyl diacetic acid or glyceryl imino diacetic acid.

Antioxidants are included in the inventive compositions in an amount of from 0.01 to 10%, preferably from 0.1 to 5%, most preferably from 0.2 to 4%. Reducing agents are included in the inventive compositions in an amount of from 0.01 to 10%, preferably from 0.1 to 5%, most preferably from 0.2 to 4%. Chelating agents are included in the inventive compositions in an amount of from 0.01 to 1%, preferably from 0.05 to 0.5%, most preferably from 0.05 to 0.3%.

Various other types of active ingredients may be present in cosmetic compositions of the present invention. Actives are defined as skin or hair benefit agents other than emollients and other than ingredients that merely improve the physical characteristics of the composition. Although not limited to this category, general examples include skin lightening agents (other than acidic skin benefit agents), sunscreens and tanning agents.

Sunscreens include those materials commonly employed to block ultraviolet light. Illustrative compounds are the derivatives of PABA, cinnamate and salicylate. For example, octyl methoxycinnamate and 2-hydroxy-4-methoxy benzophenone (also known as oxybenzone) can be used. Octyl methoxycinnamate and 2-hydroxy-4-methoxy benzophenone are commercially available under the trademarks, Parsol MCX and Benzophenone-3, respectively.

The exact amount of sunscreen employed in the emulsions can vary depending upon the degree of protection desired from the sun's UV radiation. However, the amount of sunscreens added should not compromise the high skin friction of the inventive compositions as defined previously for the emollient materials.

Another preferred optional ingredient is selected from essential fatty acids (EFAs), i.e., those fatty acids which are essential for the plasma membrane formation of all cells, in keratinocytes EFA deficiency makes cells hyperproliferative. Supplementation of EFA corrects this. EFAs also enhance lipid biosynthesis of epidermis and provide lipids for the barrier formation of the epidermis. The essential fatty acids are preferably chosen from linoleic acid, γ-linolenic acid, homo-γ-linolenic acid, columbinic acid, eicosa-(n-6,9, 13)-trienoic acid, arachidonic acid, γ-linolenic acid, timnodonic acid, hexaenoic acid and mixtures thereof.

Other optional ingredients may include coloring agents, opacifiers and pigments (e.g. titanium dioxide, silica) and perfumes. Amounts of these materials may range anywhere from 0.001% up to 20% by weight of the composition.

Use of the Composition

The composition according to the invention is intended primarily as a product for topical application to human skin, especially as an agent for lightening or depigmenting the skin, conditioning and smoothening the skin, and preventing or reducing the appearance of wrinkled or aged skin.

In use, a small quantity of the composition, for example from 1 to 5 ml, is applied to exposed areas of the skin, from a suitable container or applicator and, if necessary, it is then spread over and/or rubbed into the skin using the hand or fingers or a suitable device.

Product Form and Packaging

The composition can be packaged in a suitable container to suit its viscosity and intended use by the consumer. For example, a composition can simply be stored in a non-deformable bottle or squeeze container, such as a tube or a lidded jar.

The invention accordingly also provides a closed container containing a cosmetically acceptable composition as herein defined.

The following specific examples further illustrate the invention, but the invention is not limited thereto.

EXAMPLES

Examples 1 to 5

Examples of formulations according to the present invention are outlined in Table 1.

TABLE 1

| Ingredient Trade and CTFA Name | Phase | 1 | 2 | 3 | 4 | 5 |
|---|---|---|---|---|---|---|
| Stearic acid | A | 14.9 | 14.9 | 12.9 | 17.9 | 15.7 |
| Sodium ceteary sulfate* (Anionic emulsifiers) | A | 1.0 | 1.0 | 1.5 | 1.5 | 0.5 |
| Myrj 59* (Nonionic emulsifiers) | A | 2.0 | 1.5 | 2 | 2 | 2 |
| Span 60* (Nonionic emulsifiers) | A | 2.0 | 1.5 | 2 | 2 | 2 |
| Parsol 1789 | A | 0.40 | | 0.4 | 0.4 | 0.4 |
| Propyl paraben | A | 0.10 | 0.10 | 0.10 | 0.10 | 0.10 |
| BHT | A | 0.1 | 0.1 | 0.1 | 0.1 | 0.1 |
| Parsol MCX | A | 0.75 | | 0.75 | 0.75 | 0.75 |
| Dimethicone | A | | 0.50 | 0.75 | | 0.75 |
| Water | B | BAL* | BAL | BAL | BAL | BAL |
| EDTA | B | 0.04 | 0.04 | 0.04 | 0.04 | 0.04 |
| Pamulen TR 2 | B | | 0.10 | 0.05 | | 0.05 |
| Methyl paraben | B | 0.15 | 0.15 | 0.15 | 0.15 | 0.15 |
| Skin benefit agents | C | 3.5 | 2.0 | 2.0 | 2.0 | 2.0 |
| Humectant | C | 10 | 10 | 8 | 7 | 8 |
| TOTAL | | 100 | 100 | 100 | 100 | 100 |
| pH | | 4.5 | 4.7 | 4.6 | 4.6 | 4.7 |

*BAL = Balanced to 100

The formulations presented in Table 1 are prepared in the following fashion. Phase A is heated at 75° C. Phase B is heated to 75° C. in a container separate from that of Phase A. Thereafter the phases are combined with mixing with heat being turned off. Phase C is heated to 62° C. and mixed into Phases A/B at 62° C. The mixture is cooled until 40° C. and then packed.

Examples 6–13

A set of comparative compositions were prepared to demonstrate the special advantage of formulating to achieve a normal force value of less than −100 milli-Newton and the required viscosity ranges of a vanishing cream at defined shear rates, i.e. 10 to 75 PaS at a shear rate of $1\ s^{-1,\ 2}$ to 20 at a shear rate of $10\ s^{-1}$ and 0.6 to 5 Pas at a shear rate of $100\ s^{-1}$. For comparison, an acid soap-based vanishing cream composition (Example 6) was also prepared and its rheological properties were measured as well. The compositions, pH, and rheological properties of the comparative Examples 6–13 are listed in Table 2 below.

TABLE 2

| Ingredients | Phase | 6 acid soap base | 7 | 8 | 9 | 10 | 11 | 12 | 13 |
|---|---|---|---|---|---|---|---|---|---|
| Stearic acid | A | 17.9 | 17.9 | 17.9 | 17.9 | 17.9 | 17.9 | 17.9 | 17.9 |
| Sodium cetearyl sulfate* (Anionic emulsifiers) | A | | 2.2 | | 1 | 1.5 | 2 | 3 | 2 |
| Myrj 59* (Nonionic emulsifiers) | A | | | 2 | 2 | 2 | 2 | 2 | 1 |
| Span 60* (Nonionic emulsifiers) | A | | | 2 | 2 | 2 | 2 | 2 | 1 |
| KOH, 22% (form in situ soap with stearic acid) | | 2.20 | | | | | | | |
| Water | B | | BAL | BAL | BAL | BAL | BAL | BAL | BAL |
| Glycerin | B | | 1 | 1 | 1 | 1 | 1 | 1 | 1 |
| Weight ratio of anionic to nonionic | | N/A | 1:0 | 0:1 | 1:4 | 1.5:4 | 1:2 | 3:4 | 1:1 |
| Viscosity at r = 1 s$^{-1}$ (r = shear rate) | | 28.9 | 18 | 9.05 | 10 | 17.3 | 20.8 | 38.5 | 12.3 |
| Viscosity at r = 10 s$^{-1}$ (r = shear rate) | | 3.98 | 2.72 | 1.64 | 2.44 | 4.95 | 5.17 | 7.37 | 2.66 |
| Viscosity at r = 100 s$^{-1}$ (r = shear rate) | | 1.63 | 1.13 | 0.48 | 1.09 | 1.8 | 1.63 | 1.75 | 0.8 |
| Normal force value, milli-Newton | | −1220 | −1150 | −82 | −140 | −909 | −1800 | −1413 | −220 |
| pH | | 7.5 | 4.5 | 4.5 | 4.5 | 4.5 | 4.5 | 4.5 | 4.5 |

*BAL = Balanced to 100

Normal forces and viscosity were measured using a controlled strain rheometer which a shearing force capability and normal force transducer (e.g. ARES (Advanced Rheometric Expansion System) from Rheometrics Corporation. Normal force measurements appearing under Table 2 as well as those in the subsequent Example were measured in the following manner. Samples were compressed between parallel plates of diameter of 25 mm and gap of 100 micron. Measurements were made in a shear sweep mode with a shear rate range from 0 to 10,000 sec$^{-1}$. The normal stress value was calculated as the difference between the force at zero shear rate and force at highest shear rate. Measurements were conducted at room temperature 25° C.

Sensory evaluation of the preferred examples listed in Table 1 and 2 by expert panelists were proven to be matching the vanishing cream made from the acid-soap.

Example 14

This example demonstrates a typical composition outside of the present invention having positive normal force and viscosity profiles at the defined shear rates outside of a vanishing cream's. The composition is listed in Table 3.

TABLE 3*

| | Wt % | Phase |
|---|---|---|
| water, DI | 57.91 | A |
| disodium EDTA | 0.05 | A |
| magnesium aluminum silicate | 0.6 | A |
| methyl paraben | 0.15 | A |
| simethicone | 0.01 | A |
| butylene glycol 1,3 | 3.0 | A |
| hydroxyethylcellulose | 0.5 | A |
| glycerine, USP | 2.0 | A |
| xanthan gum | 0.2 | A |
| triethanolamine | 1.2 | B |

TABLE 3*-continued

| | Wt % | Phase |
|---|---|---|
| stearic acid | 3.0 | B |
| propyl paraben NF | 0.1 | B |
| glyceryl hydroxystearate | 1.5 | B |
| stearyl alcohol | 1.5 | B |
| isostearyl palmitate | 6.0 | B |
| C12–15 alcohols octanoate | 3.0 | B |
| dimethicone | 1.0 | B |
| cholesterol NF | 0.5 | B |
| sorbitan stearate | 1.0 | B |
| butylated hydroxytoluene | 0.05 | B |
| tocopheryl acetate | 0.1 | B |
| PEG-100 stearate | 2.0 | B |
| sodium stearoyl lactylate | 0.5 | B |
| hydroxycaprylic acid | 0.1 | C |
| glycolic acid, 70% | 11.43 | C |
| ammonium hydroxide | 2.4 | C |
| alpha-bisabolol | 0.2 | C |

*The composition has pH = 3.8.

The compositions of Example 14, Table 3, were prepared as follows:

1. Heat Phase A to 80° C.
2. Heat Phase B to 75° C. in a separate container
3. Add B to A and mix with heat off for 30 min.
4. At 50° C. add Phase C and mix for 10 min.

Table 4 lists the normal force and viscosity values for the composition of Example 14.

TABLE 4

|  | Normal force, Milli-Newton | Viscosity, Pas | | |
| --- | --- | --- | --- | --- |
|  |  | at 1 s⁻¹ | at 10 s⁻¹ | at 100 s⁻¹ |
| Example 14 | +160 | 92 | 11 | 1.63 |

As shown in Table 4, the composition of Example 14 has a positive normal force because it has insufficient stearic acid level and a high oil to stearic acid ratio, which is outside the scope of this invention, as shown in Table 3.

It will be understood that the embodiments described herein are merely exemplary and that a person skilled in the art may make many variations and modifications without departing from the spirit and scope of the invention. Thus, all such variations and modifications are intended to be included within the scope of the invention as defined in the appended claims.

What is claimed is:

1. A cosmetic composition comprising:
   (a) at least about 4% by weight of the composition of solid asymmetric particles;
   (b) an anionic emulsifier selected from the group consisting of alkyl sulphates, aralkyl sulphates, alkyl ethoxy ether sulphates, alkaryl sulphonates, alkyl succinates, alkyl sulphosuccinates, N-alkoyl sarcosinates, isethionates, N-acyl taurate, fatty acid amides of methyl tauride and combinations thereof; and
   (c) a cosmetically acceptable vehicle;
   wherein the pH of the composition is less than about 5.7 and
   wherein the composition has a normal stress of less than minus about 100 milli-Newtons;
   wherein the viscosity of the composition is about 10 Pas to about 75 Pas, about 2 Pas to about 25 Pas and about 0.5 Pas to about 6 Pas at shear rates of $1\ s^{-1}$, $10\ s^{-1}$ and $100\ s^{-1}$, respectively; and
   wherein said composition is a leave-on composition.

2. The composition of claim 1, further comprising a nonionic emulsifier.

3. The composition of claim 2, wherein the nonionic emulsifier is selected from the group consisting of sorbitan ester, ethoxylated sorbitan ester, ethoxylated alky ether, ethoxylated fatty acid ether, fatty alcohol, ethoxylated fatty alcohol and ester of glycerin and fatty acid.

4. The composition of claim 2, wherein the ratio of anionic emulsifier to nonionic emulsifer is in the range of about 1:0.0000001 to about 1:9.

5. The composition of claim 1, wherein said anionic emulsifier remains anionic at low pH.

6. The composition of claim 1, wherein said anionic emulsifier is present in an amount of about 0.1% to about 10% by weight of said composition.

7. The composition of claim 2, wherein a ratio of said anionic emulsifier to said nonionic emulsifier is set such that said composition exhibits viscosity profiles of 10 to 75 Pas, 2 to 25 Pas and 0.5 to 6 Pas at the shear rates of 1 s, $10\ s^{-1}$ and $100\ s^{-1}$, respectively; wherein the composition has a normal stress of less than minus about 100 milli-Newtons.

8. The compositions of claim 1, wherein said solid asymmetric particles comprise about 10% to about 25% by weight of said composition.

9. The compositions of claim 1, wherein said solid asymmetric particles comprise about 12% to about 20% by weight of said composition.

10. The composition of claim 1, wherein the solid asymmetric particles are crystalline.

11. The composition of claim 1 wherein the solid asymmetric particles are selected from the group consisting of fatty acid particles, mica, talc, clays and mixtures thereof.

12. The composition of claim 1 wherein the solid asymmetric particles are particles of a fatty acid containing from 12 to 22 carbon atoms.

13. The composition of claim 1 further comprising an acidic skin benefit agent.

14. The composition of claim 13 wherein the amount of said acidic skin benefit agent is at least about 0.0001% by weight of the composition.

15. The composition of claim 13 wherein the acidic skin benefit agent is selected from the group consisting of alpha-hydroxy acids, beta-hydroxy acids, poly-hydroxy acids, skin lightening agents, and mixtures thereof.

16. The composition of claim 13 wherein said acidic skin benefit agent is selected from the group consisting of glycolic acid, lactic acid, 2-hydroxyoctanoic acid, salicylic acid, ferulic acid, sebacic acid, and combinations thereof.

17. The composition of claim 1 wherein the solid asymmetric particles are particles of stearic acid.

18. A cosmetic composition comprising:
   (a) about 10% to about 25% by weight of the composition of solid asymmetric particles; wherein said particles are stearic acid;
   (b) about 0.5% to about 5% by weight of the composition of an anionic emulsifier selected from the group consisting of alkyl sulphates, aralkyl sulphates, alkyl ethoxy ether sulphates, alkaryl sulphonates, alkyl succinates, alkyl sulphosuccinates, N-alkoyl sarcosinates, isethionates, N-acyl taurate, fatty acid amides of methyl tauride and combinations thereof;
   (a) a non-ionic surfactant; and
   (b) a cosmetically acceptable vehicle;
   wherein the pH of the composition is less than about 5.7;
   wherein the composition has a normal stress of less than minus about 100 milli-Newtons;
   wherein the viscosity of the composition is about 10 Pas to about 75 Pas, about 2 Pas to about 25 Pas and about 0.5 Pas to about 6 Pas at the shear rates of $1\ s^{-1}$, $10\ s^{-1}$ and $100\ s^{-1}$, respectively;
   wherein the ratio of said anionic surfactant to said non-ionic surfactant is about 3:2 to about 1:7; and
   wherein the composition is a vanishing cream.

* * * * *